United States Patent [19]  
Denckla

[11] 3,962,058  
[45] June 8, 1976

[54] FLAT BED ISOELECTRIC FOCUSING DEVICE

[75] Inventor: William Donner Denckla, Tenafly, N.J.

[73] Assignee: Hoffmann-La Roche Inc., Nutley, N.J.

[22] Filed: Apr. 24, 1975

[21] Appl. No.: 571,161

[52] U.S. Cl. .......................... 204/180 R; 204/299 R
[51] Int. Cl.² .................. G01N 27/40; G01N 27/26
[58] Field of Search............ 204/299, 180 R, 180 G

[56] References Cited
UNITED STATES PATENTS
3,616,456   10/1971   Valumet ............................ 204/299

Primary Examiner—John H. Mack
Assistant Examiner—A. C. Prescott
Attorney, Agent, or Firm—Samuel L. Welt; George M. Gould

[57] ABSTRACT

A flat bed isoelectric focusing device is described. Such device is designed to utilize small volumes, i.e., about 6 ml. and incorporates several critical construction parameters which allow for effecient separations. Thus, the liquid height should be about 2 mm and no more than 4 mm and the length to width ratio must be 15:1 or greater.

14 Claims, 1 Drawing Figure

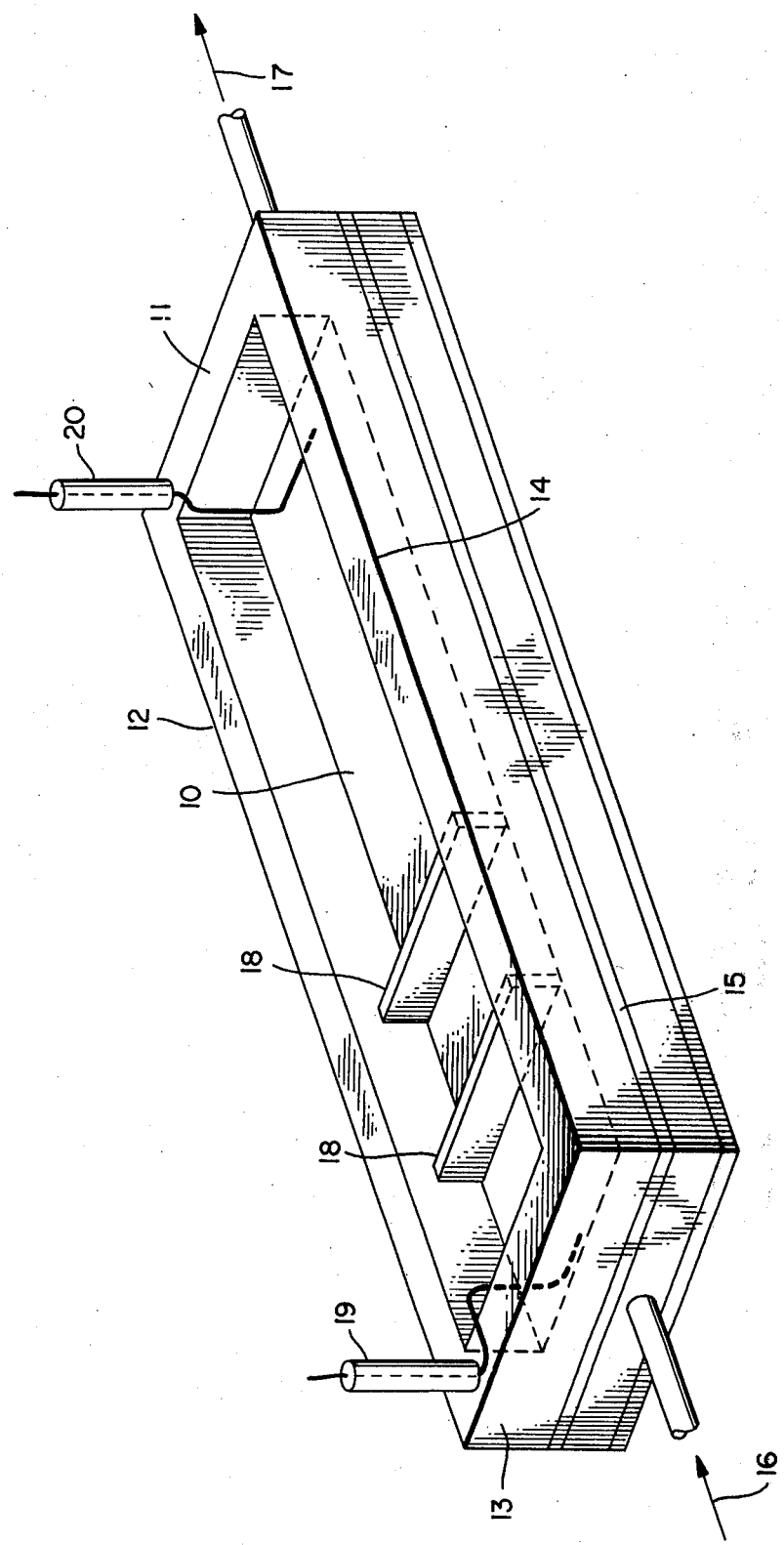

FLAT BED ISOELECTRIC FOCUSING DEVICE

BACKGROUND OF THE INVENTION

Isoelectric focusing is a useful technique for separating proteins and polypeptides in solution. This technique utilizes the fact that such compounds are zwitterions and thus have a definite pH at which they carry no net charge (isoelectric point). At their isoelectric point proteins and polypeptides will not migrate in an electric field. It has thus been possible to separate proteins and polypeptides by establishing a pH gradient with small molecular weight zwitterions (carrier ampholytes) in an isoelectric focusing device since the compunds will migrate to their characteristic isoelectric point and stop in such a gradient.

However, there have been restrictions on the size of samples which can be separated by previously available devices. The smallest devices required at least about 20 ml. of sample volume. Such volumes are too large when only small amounts of the protein or polypeptide are available since dilution would result in unacceptably low concentrations for analysis.

Smaller volume devices were particularly prone to problems arising from the phenomenon of electro-osmotic flow. This relatively large volume flow of water from one electrode to the other will cause the compounds being separated to migrate from their true isoelectric points. When the compound has a relatively weak charge density such migration can be quite extensive until the charge on the compound provides an electrostatic force sufficient to offset the force of the osmotic flow. In addition, the osmotic flow will occur mainly in the center of the channel and will fall off rapidly towards the sides. This will cause the concentration gradient to be bullet shaped and thus will not be normal to the long axis as desired for maximum resolution. Such distortion is proportionately greater in the smaller volume devices and thus prevents such small volume devices to function effectively as an analytical or preparative instrument.

One method which has been employed in the art to separate small amounts of proteins or polypeptides is to utilize a stationary support phase for the compound solution. Thus only a thin liquid film is present and the effects of electro-osmotic flow are not critical. However, these support materials such as acrylamide gel, sephadex and the like are quite expensive. Furthermore, separations on such devices are comparatively slow and recovery of the separated compounds is either laborious or not possible at all.

DESCRIPTION OF THE INVENTION

The present invention relates to a flat bed isoelectric focusing device capable of separating small volumes of proteins and polypeptides in a rapid and highly efficient manner. In a preferred embodiment, the device of the present invention may be designed to utilize volumes of less than 10 ml. The deleterious effects of electro-osmotic flow are minimized by employing critical dimensional parameters.

It has now been found that small volume isoelectrical focusing devices can be constructed by utilizing a long, narrow trough shape in the compartment containing the protein or polypeptide solution. Critical dimensions to be considered in such construction are the length to width ratio which must be 15:1 to 1, or greater and the height of the water film which should be less than 4 mm and preferably about 2mm (the lower limit is set by the surface tension of the solution).

The flat bed isoelectric focusing device of the present invention will be more clearly understood by reference to the Drawing.

A rectangular separation chamber 10 is defined by four side walls 11, 12, 13 and 14. Walls 11 and 13 are the "short" walls while walls 12 and 14 are the "long" walls. The dimensions of these walls are selected so that the internal length of chamber 10 to the internal width of that chamber are in a ratio of greater than 15:1, preferably 30:1 or greater. The walls may be made of any rigid, non-conductive material which is impervious to water. Plastic materials such as acrylics, polystyrene, polypropylene, etc. are suitably employed for this purpose. The precise method of construction is not critical and thus all four walls may be molded or cast as a single piece or alternatively may be joined by cementing the individual walls together utilizing a suitable adhesive.

In order to provide the critical water height dimension needed to help minimize electro-osmotic flow effects the side walls will have a height of about 2 to 4 mm, preferably about 2mm. Increasing the height of the walls above the 2 mm level appears to slow the speed of separation of the sample into its components. Thus, a representative protein, cytochrome C, took approximately 10 times longer to reach its isoelectric point in a device having 4 mm high end walls than in a device having 2mm high end walls. By using the 2 mm walls the water in the separation chamber had a cross-sectional area which was geometrically linear and constant.

The bottom wall 15 of the device is preferably constructed out of a glass plate to provide good heat exchange. In order to maximize such heat exchange the bottom wall can be made a part of a hollow glass block through which cooling water or other heat exchange medium can be circulated, i.e., through inlet means 16 and outlet means 17.

In order to prevent rapid flow through the device and in order to facilitate recovery of the separated components it is desirable to introduce a series of baffles 18 symmetrically spaced in a plane perpendicular to the longitudinal axis of the separation chamber. These baffles are affixed to the bottom wall 15 either as an integral part thereof or by cementing individual baffle members to such bottom wall in a manner known per se. The baffles will extend from side wall 12 to side wall 14 and will have a height of one-half that of the side walls, i.e., preferably about 1 mm.

Introduction of the baffles serves to sharpen the zones of the separated components and helps prevent tailing. In operation one can observe sample proteins forming clearly visible bands whose borders are perpendicular to the longitudinal axis. This observation demonstrates that the pH gradient is formed in a symmetrical linear fashion. The number of baffles used controls the degree to which one can subdivide the pH gradient. Generally 10 or more baffles may be employed although only 2 baffles have been shown in the Drawing for clarity and simplicity of representation. Since a balance must be achieved between increasing the discrimination by using more baffles and the increased difficulty in construction caused by numerous baffles it is preferred to employ about twenty baffles.

In a further embodiment not exemplified in the Drawing it is desirable to employ a cover of appropriate dimensions to help evaporation from the separation chamber during operation. Such cover may be provided with a series of baffles which are arranged symmetrically along the longitudinal axis of the cover. These baffles would be spared so that they would alternate with the aforementioned baffles 18 in the bottom wall. The cover baffles would have the same height dimension as the bottom baffles. Use of the cover baffles serves as a further means to sharpen the separated component zones into smaller volumes in the device thereby increasing the peak height to width ratio of the component distribution.

The electrical potential needed to effect the electrophroetic separation is povided by electrode means 19 and 20. These electrode means are connected to conventional high voltage power supply source by conductive means forming a circuit in the usual manner and not show in the Drawing.

In a preferred embodiment the electrode means comprise conductive metal wire electrodes most preferably platinum wire electrodes. Additionally, it is desirable that the electrode compartment defined by the area between the respective electrodes and the first baffles be kept as small as practical.

Operation of a representative flat bed isoelectric focusing device of the present invention is presented below for additional clarification. Such device has a separation chamber volume of 6 ml. with internal dimensions as follows: length 300 mm; width 10 mm; height 2 mm. The separation chamber is equipped with 20 baffles each having a height of 1 mm. Evaporation is prevented by a cover.

The electrode compartments are filled with distilled water and then the component solution, i.e., 1% protein in water (w/v) containing the carrier ampholytes are poured into the separation chamber. A voltage of 1,000 volts is introduced and for a run utilizing a pH gradient of 3-10 a total time of about 3 hours is needed to complete the separation. Generally, the end of the run can be determined when a constant low conductance is observed indicating that all the ampholytes have reached their isoelectric points and thus have a minimal charge.

In order to preserve the integrity of the separated components, the compartments formed by the spaces between the various baffles should be evacuated simultaneously. This can be conveniently carried out by using an evacuation instrument designed for this purpose. Such evacuation instrument comprises a number of flexible tubes, the number being at least equal to the number of compartments formed in the separation chamber by the bottom baffles, fitted with suction end means, i.e., nozzles or tips of reduced volume. Each of these tubes leads to separate storage reservoirs which in turn are linked to a common vacuum source by an appropriate manifold. The tubes are introduced into the separation chamber after the separation has been completed and the voltage removed from the device. Upon activating the vacuum source the liquid from each compartment is simultaneously removed in segregated manner and stored independently for further analytical or preparative workup as desired.

I claim:

1. A flat bed isoelectric focusing device comprising a rectangular separation chamber defined by two side walls, two end walls and a bottom wall wherein the length to width rates of said separation chamber is at least 15:1 and the height of said side and end walls is from 2 to 4 mm; said bottom wall being provided with at least ten symmetrically spaced baffle means, said baffle means extending from one side wall to the other in a plane perpendicular to the longitudinal axis of said separation chamber and having a height of about ½ the height of said side and end walls; and electrode means in operative relationship with said separaton chamber.

2. The device of claim 1 wherein the said length to width ratio of said separation chamber is at least 30:1.

3. The device of claim 1 wherein the height of said side and end walls is about 2 mm.

4. The device of claim 1 wherein twenty baffles are provided.

5. The device of claim 1 wherein the said side and end walls are made of a rigid plastic and the bottom wall is glass.

6. The device of claim 5 wherein said bottom wall comprises a heat exchange means.

7. The device of claim 1 wherein the total volume of said separation chamber is less than 10 ml.

8. The device of claim 1 wherein a cover means is provided during operation to prevent evaporation.

9. The device of claim 8 wherein said cover means is provided with a number of baffle means having a height of ½ the height of said side and end walls, said baffle means being so arranged and constructed as to be in alternating relationship with the said baffle means on said bottom wall.

10. A method for the isoelectric focusing of a solution of 10 ml. volume or less, said solution containing substances which will migrate under the influence of an applied potential, which method comprises introducing said solution into the separation chamber of a device of claim 1; providing a desired pH gradient across said separation chamber by utilizing carrier ampholytes; providing a potential field across said separation chamber whereby said substances will migrate to their respective isoelectric points and form distinct substance zones; and withdrawing said substances from their respective zones simultaneously and in a segregated manner.

11. The method of claim 10 wherein said solution comprises one or more proteins and said carrier ampholyte.

12. The method of claim 11 wherein said protein is present in a concentration of about 1% (w/v).

13. The method of claim 10 wherein said potential is applied until a constant low conductance is observed.

14. The method of claim 10 wherein heat exchange is provided during the period of isoelectric focusing.

* * * * *

UNITED STATES PATENT AND TRADEMARK OFFICE
CERTIFICATE OF CORRECTION

PATENT NO. : 3,962,058

DATED : June 8, 1976

INVENTOR(S) : William Donner Denckla

It is certified that error appears in the above-identified patent and that said Letters Patent are hereby corrected as shown below:

Column 4, line 7, of claim 1 "rates" should be : ratio

*Signed and Sealed this*

*Thirteenth* Day of *September 1977*

[SEAL]

Attest:

RUTH C. MASON
*Attesting Officer*

LUTRELLE F. PARKER
*Acting Commissioner of Patents and Trademarks*